United States Patent [19]

Rizk et al.

[11] 4,181,594

[45] Jan. 1, 1980

[54] MATRIX RECOVERY ELECTROPHORESIS APPARATUS

[75] Inventors: Nabil I. Rizk, Gibsonia; Frank Valentich, Pittsburgh, both of Pa.

[73] Assignee: University of Pittsburgh, Pittsburgh, Pa. ; a part interest

[21] Appl. No.: 24,419

[22] Filed: Mar. 27, 1979

[51] Int. Cl.[2] ............................................. G01N 27/28
[52] U.S. Cl. ............................ 204/299 R; 204/180 G
[58] Field of Search ............ 204/180 R, 180 G, 299 R; 424/12; 23/230 B

[56] References Cited

U.S. PATENT DOCUMENTS

| | | | |
|---|---|---|---|
| 3,482,943 | 12/1969 | Csizmas et al. | 204/299 X |
| 3,674,678 | 7/1972 | Post, Jr. et al. | 204/299 |
| 3,773,646 | 11/1973 | Mandle et al. | 204/299 |
| 3,888,759 | 6/1975 | Elson et al. | 204/299 |
| 3,932,229 | 1/1976 | Grandine | 204/180 G |
| 3,951,776 | 4/1976 | Eibl et al. | 204/299 |

Primary Examiner—Arthur C. Prescott
Attorney, Agent, or Firm—Arnold B. Silverman

[57] ABSTRACT

Electrophoresis apparatus including a cooperating gel slab and matrix member. The matrix member has a first surface in generally surface-to-surface contact with the gel and is positioned overlying the gel. The matrix member has a plurality of openings therein which cooperate with the gel member to define a series of upwardly open wells. Electrode means pass through the wells. A reservoir for providing buffer solution to the gel is provided in underlying relationship with respect to the matrix member-gel slab assembly. The matrix member-gel slab assembly are urged into intimate contact. In a preferred form, integrally formed channel means cooperate with the underlying slab and a pump to establish a vacuum which serves to urge the matrix member-gel slab into intimate contact.

The reservoir may have a support bracket for securing the matrix member-gel slab in overlying relationship to a buffer solution containing trough so that the matrix member-gel slab is maintained in generally horizontal position. In this fashion the material to be separated, such as proteins, migrates upward from inside the gel into the overlying wells. A plurality of molecules separated previously as by a standard slap gel system, for example, are eluted into separate wells.

19 Claims, 9 Drawing Figures

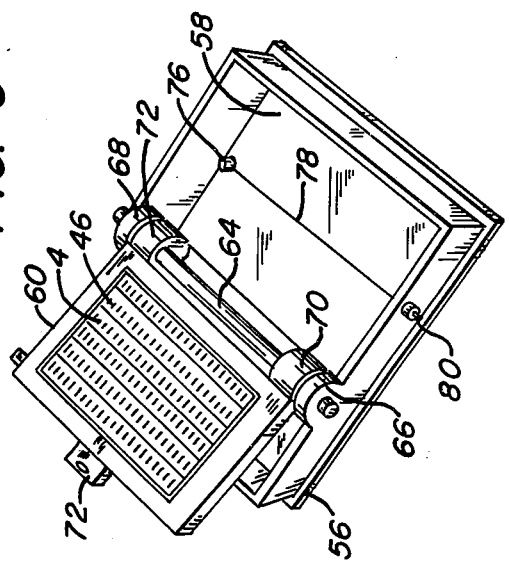
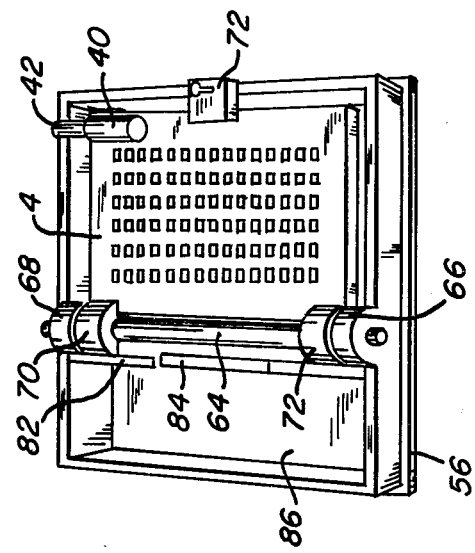

MATRIX RECOVERY ELECTROPHORESIS APPARATUS

BACKGROUND OF THE INVENTION

1. Field of the Invention

This invention relates to electrophoresis apparatus and, more specifically, it relates to an improved form of plate-like electrophoresis apparatus for the recovery of material from gel.

2. Description of the Prior Art

It has long been known to employ electrophoresis as a means for effecting separation of materials in a solution. For example, migration of protein molecules, suspended particles or colloidal particles toward an electrode of opposite charge has been the basis for effecting such separation. It has also been known to employ gels in such procedures. Molecules move through a gel under the influence of a voltage gradient at a velocity inversely related to their molecular weight.

The study of proteins through the use of polyacrylamide gel, agar and other types of gels by electrophoresis has been known. In this procedure proteins move through a gel under the influence of a voltage gradient at a velocity generally inversely related to their molecular weight. This provides a technique for separating proteins of varying molecular weights for their eventual isolation and characterization. Staining the gels or the use of incorporated radioactivity in the proteins to permit the recordings of autoradiograms has allowed for characterization of protein species and their distribution within a particular biological system. The recovery of the individual proteins associated with the various gel bands has, however, left something to be desired. Generally the gel strips are cut into either given length segments or into segments each of which contains one band and attempts are made to elute the proteins incorporated in the segments. In such a procedure the technique becomes time consuming as well as cumbersome as it relies on diffusion for the elution of the protein. Generally, such a method entails considerable dilution of the protein as well. Attempts have been made to electrophorese the material directly out of the gel employing cellophane support of the gel. Elution of the material continuously yields very high dilutions and also ambiguous results if more than one band comes under the influence of the field simultaneously.

U.S. Pat. No. 3,699,033 discloses an electrophoresis system wherein tubes contain gel which is positioned around a centrally disposed core. U.S. Pat. No. 3,384,564 discloses a tube gel electrophoresis system which provides an upper reservoir of buffer solution with an electrode and a lower buffer solution with an electrode. These reservoirs are connected by tubes which contain different gels. This patent seeks to obtain benefits from the difference in porosity of the various gels employed in the tubes. U.S. Pat. No. 3,616,454 discloses the use of polyacrylamide gel columns wherein the specimen is introduced at the upper end and the lower end terminates in a container of elution solution.

U.S. Pat. No. 4,048,049 discloses a tube gel electrophoresis system wherein a divided container has a number of gel tubes which are generally vertically oriented and provide communication between an upper buffer chamber and a lower buffer chamber.

U.S. Pat. No. 3,956,099 discloses a rather complex system which is adapted for continuous operation. The system is multicelled and contemplates delivery of the components into a plurality of membrane bags from an array of separating cells.

U.S. Pat. No. 3,305,471 discloses a rather complicated system wherein a separating chamber is defined by two glass plates.

U.S. Pat. No. 3,932,265 discloses a gel system for separation of molecules according to molecular weight, shape or charge. The material separated remains in the gel after processing.

U.S. Pat. No. 3,989,612 discloses a mechanical assembly of extracted segments of gel. It contemplates a plurality of different band sectors of gel. It also contemplates physical isolation of the bands and the use of electrophoresis to remove the factions contained within the specific bands.

In spite of the existence of these prior known systems, there remains a need for an improved gel electrophoresis system which will provide the desired separation in rapid fashion and produce reliable resluts while avoiding undesired high dilutions.

SUMMARY OF THE PRESENT INVENTION

The above described need has been met by the present invention. The present invention provides a gel slab in combination with a matrix member having a first surface in surface-to-surface contact with the gel slab. The matrix member has a plurality of openings which cooperate with the gel slab to define a number of upwardly open wells. Means are provided for urging the matrix member and gel slab into intimate contact. Electrode means pass through the wells and electrical means energize the same. Reservoir means are provided for establishing contact between the gel and a buffer solution. A buffer solution is provided in the overlying wells and the separate constituents travel through the gel into the wells.

A preferred form of means for urging the gel slab into intimate contact with the matrix member includes providing a series of integrally formed channels in the matrix member. These cooperate with the gel means to define passageways which by means of pump means are evacuated so as to create pressure differentials which urge the two members into intimate contact.

It is an object of this invention to provide a gel electrophoresis recovery system which will provide rapid and accurate results.

It is another object of this invention to provide such apparatus wherein undesired high dilutions are avoided.

It is another object of this invention to provide such apparatus wherein a plurality of independent wells are provided for receiving a plurality of proteins or other materials from the gel independently.

It is another object of this invention to provide such apparatus which is economical to manufacture and employ.

It is another object of this invention to provide such apparatus wherein the need to employ a membrane, such as cellophane, for support of the gel is eliminated.

It is another object of this invention to provide an apparatus which is so oriented as to permit vertical migration of proteins or other molecules.

It is another object of this invention to provide such apparatus in a fashion which resists formation of undesired bubbles during electrophoresis.

It is another object of this invention to provide an electrophoresis system wherein each of the wells has its own electrode and thereby performs as a separate system.

These and other objects of the invention will be more fully understood from the following description of the invention on reference to the illustrations appended hereto.

BRIEF DESCRIPTION OF THE DRAWINGS

FIG. 5 shows the matrix member-gel slab assembly in combination with the reservoir means with the assembly in position to receive buffer solution from the trough portion of the reservoir means.

FIG. 6 is a figure similar to FIG. 5 except showing the matrix member-gel slab in a different position.

DESCRIPTION OF THE PREFERRED EMBODIMENTS

As used herein, unless the adjacent text expressly and clearly indicates a contrary intention, the term "matrix member" will refer to a member which cooperates with a gel slab and has a plurality of openings adapted to contain buffer solution and each such opening provided with an electrode.

Figure 2:
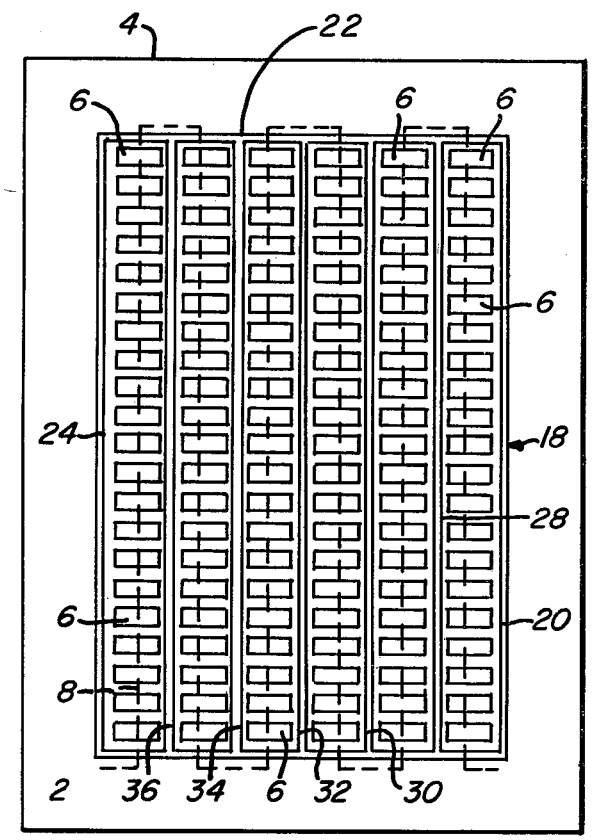
FIG. 2 is a bottom plan view of the matrix member.
Figure 1:
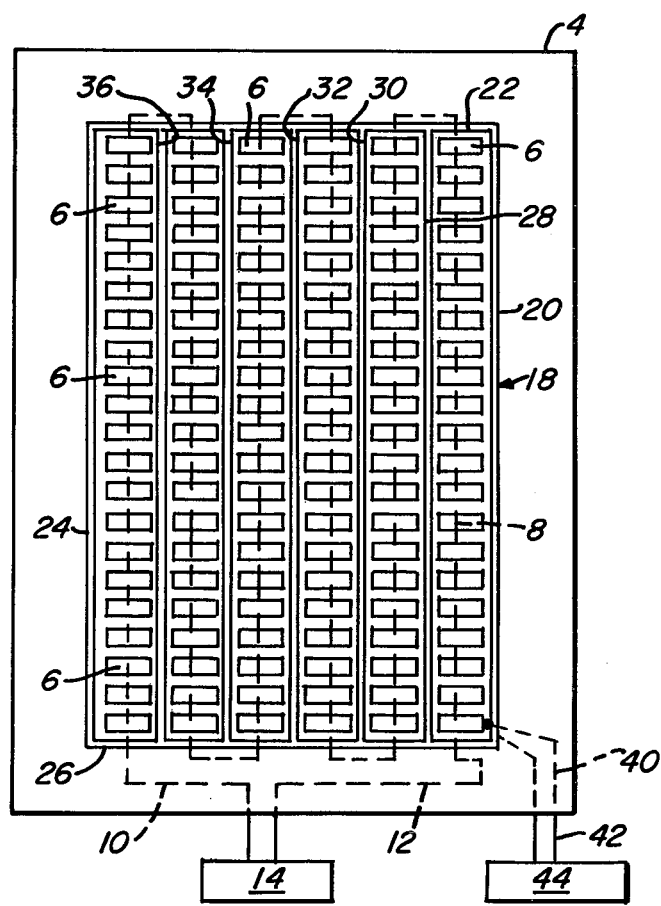
FIG. 1 is a partially schematic bottom plan view of a portion of the invention showing the matrix member and portions of the cooperating equipment.

Referring now to FIGS. 1 and 2 in greater detail, there is shown a preferred form of matrix member 4 which is provided with a plurality of openings 6 which extend entirely through the matrix member 4. In the form shown, the openings 6 are provided in six rows which are oriented generally parallel with respect to each other. In the form shown, openings 6 of one row are also aligned with openings of other rows. Each opening 6 is provided with an electrode by means of electrical wire 8 which runs continuously through the entire array of openings 6 and has ends 10 and 12 operatively associated with electrical power supply 14 which may be any conventional means of providing power to the system. The preferred alternating current may be in the form of square wave with available duty cycle ranging from 0.1% to 99.9% and the positive peak and the negative peak independently adjustable. Due to the large varieties of molecules encountered in electrophoresis, a wide range of voltages may be employed advantageously.

As a general purpose, a voltage of about 0–600 volts and a current of 0–1000 mA may be employed for electrophoresis and recovery. For isoelectric focusing about 0–5 Kv at 0–5 mA is desirable at a duty cycle of 99.99%, for example. In the preferred form the system will be energized by alternating current of a voltage of about 0 to 50 volts.

As in a preferred embodiment the wells are of relatively small volume, it is preferred to use a low duty cycle alternating current having a net direct current equivalent to that required to extract the material from the gel. This serves to resist undesired change in pH by taking advantage of the difference in mobility of the hydronium ion and the organic molecule under investigation to allow for recombination of the hydronium and hydroxyl ions to maintain the desired pH of the buffer.

Using alternating current of low duty cycle will allow the hydronium ion (the small ions responsible for the pH change) to migrate in the opposite direction from the molecule and restore the original pH. In effect this is equivalent to DC electrophoresis plus a neutralizing cycle for the gradient built up during that cycle. Due to the fact that hydronium ions ($H_3O+$) is much smaller than any organic molecule under investigation, the duty cycle for the neutralization may be of very short duration, i.e. a low duty cycle.

As a preferred means of securing the matrix member to a gel slab it is desired to establish a pressure differential by imposing a vacuum on the pair of superposed members. The vacuum may advantageously be relatively low such as a few inches of mercury if desired. While this will be discussed in greater detail hereinafter, it should be noted that integrally formed within the undersurface of matrix member 4 are a series of channels 18, which cooperate with the gel slab to define a series of passageways. These channels are interconnected and generally surround all of the openings 6. It is noted that around the perimeter channels 20, 22, 24 and 26 are connected to each other. Similarly, channels 28, 30, 32, 34, 36 divide adjacent rows of openings 6 and are in communication at their ends respectively with channel portions 22, 26. If desired, additional transverse channels (not shown) may be provided in addition to and between channels 22, 26. These additional channels may connect two or more channels 20, 28, 30, 32, 34, 36, 24. Channel extension 40 connects the channel network with conduit 42 which in turn is connected to pump 44. When the pump 44 is turned on, it pumps air out of the assembly thereby creating partial vacuum within the conduits and permitting atmospheric pressure to urge the matrix member 4 into intimate surface-to-surface contact with the underlying gel slab. In the form shown a major portion of channels 18, 40 are spaced inwardly from the marginal edges of matrix member.

While the matrix members 4 can be made from a number of different materials it is preferred that it be made from materials which are transparent, electrically insulative and of relatively high strength. A suitable material is polycarbonate. The matrix member may advantageously be made by injection molding. The matrix member preferably has a thickness of about 5 mm to 24 mm.

Figure 3:
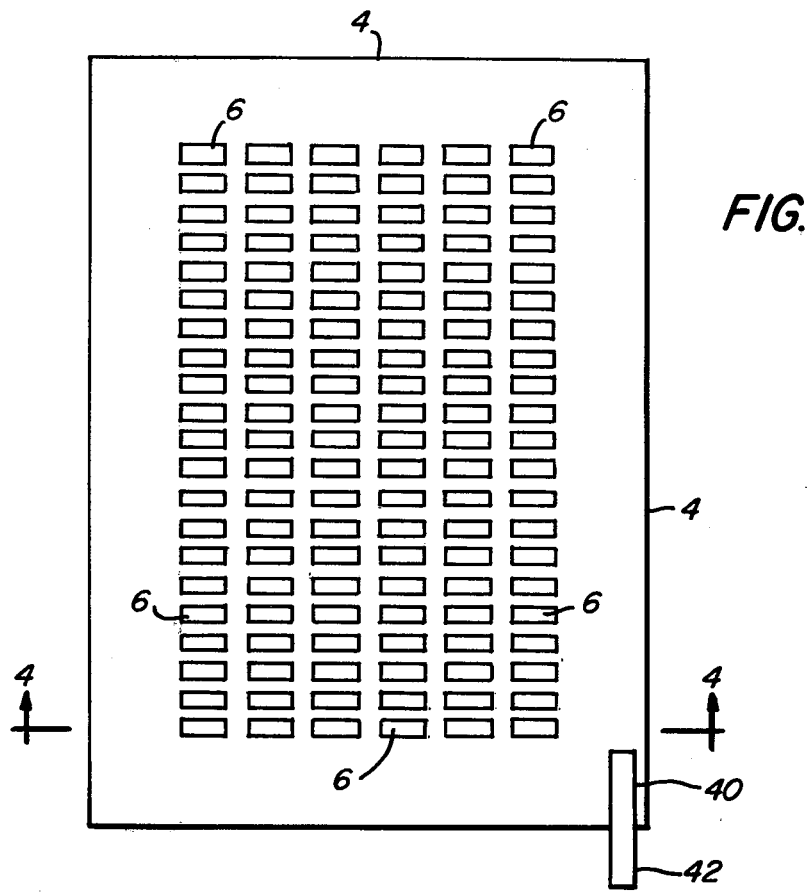
FIG. 3 is a top plan view of the matrix member.

Referring now to FIG. 3, there is shown a top plan view of a matrix member 4. As the channel 18, in the form shown, is provided by forming it in the lower portion or lower surface of the matrix member 4, it is not visible in the top plan view.

In the form shown in FIG. 3, the matrix member 4 has six rows of openings 6 each of which has 21 openings. It will be appreciated that the matrix member 4 may be provided with a wide variety of numbers of openings 6 depending upon the desired number of wells and arrangement thereof.

Figure 4:
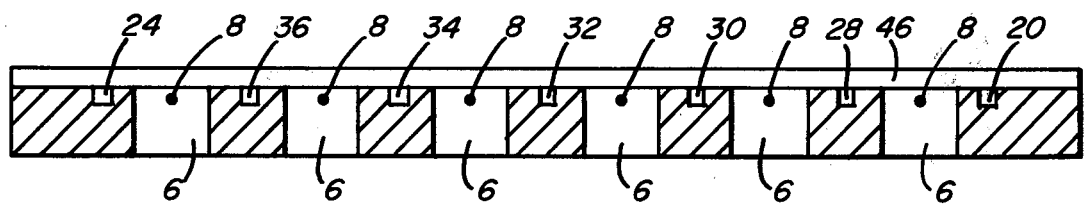
FIG. 4 is a cross sectional illustration of the apparatus taken through 4—4 of FIG. 1 but showing in addition the gel layer in position.
Figure 4A:
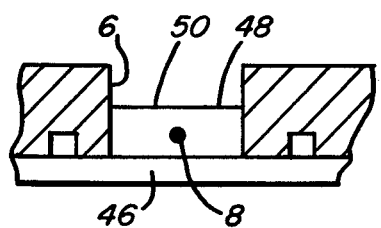
FIG. 4a is a fragmentary, partially schematic cross-sectional illustration of a portion of the apparatus of FIG. 4 inverted for clarity of illustration.

Referring now to FIG. 4 there is shown a section taken through 4—4 of FIG. 3 except that in FIG. 4 it is shown with the overlying gel slab 46. It will be appreciated that the openings 6 cooperate with the overlying slab 46 to establish a series of wells which may be indicated generally by the well 48 shown in FIG. 4a which is defined by the opening 6 and the gel slab 46. It is noted that each of the wells formed by cooperation with the opening 6 and slab 46 defines a discreet cell which has its own electrode 8 which really is a segment of the electrode 8 which passes through the series of wells. It will be appreciated that when the matrix member is positioned in overlying relationship with respect to the gel slab 46 each of the wells may be provided with a liquid buffer 50 such as that indicated in well 48 shown in FIG. 4a.

EXAMPLE

By way of an example of a form of apparatus suitable for the above-described preferred embodiment the gel slab 46 is preferably a polyacrylamide gel which is about 10 centimeters by 12 centimeters with a thickness of about 1 to 3 mm. The matrix member 4 is composed of Plexiglas and has six rows of twenty-one rectangular openings 6 with each opening being 0.8 mm by 0.3 mm and the full depth of the sheet 3/4 mm thick (the thickness is preferably about 5 mm to 24 mm). The matrix member 6 has outer dimensions of 3½ inch by 4½ inch, with the openings about 0.5 cm center to center. The wells will have a total volume of over 0.5 ml of eluting buffer. The channel 18 is 5 millimeters deep and 1 millimeter wide. The pump is an aspirator pump. Each well has been filled with eluting buffer. A voltage gradient of 50 volts is imposed. In operating the system, proteins or other molecules will, under the influence of a voltage differential, migrate upward through gel 46 and enter the individual wells 48 wherein under the influence of the voltage gradient established by upper platinum electrode 8, separation will be effected in each discreet well 48. In about fifteen minutes the electrophoresis is stopped and the solution in each well containing the eluted molecules is pipetted out of the wells.

As it will be noted that the travel of the proteins or other molecules is generally vertically upwardly, the potential problem of undesired bubbles forming is effectively eliminated.

Referring now to FIGS. 5 and 6, a form of cooperating reservoir means 56 will now be considered. The gel, after it has been loaded in a standard electrophoresis procedure and the separation has been accomplished by standard (DC) or modified (AC) electrophoresis, is then placed on the bottom of the matrix member 4 (FIG. 4a) and the vacuum is applied in order to hold the gel in place. The reservoir trough 58 is filled with eluting buffer, then the gel is lowered by angular motion into the buffer. Now each well is filled as by an auto-pipette, with eluting buffer and the electrophoresis is started. It is seen that the matrix member-gel slab assembly 60 is hinged by means of hinge pin 64 which passes through bracket extension 70, 72 into journals 66, 68. By manual engagement with handle 72 which is provided with a leveling screw for adjusting the degree of immersion of the assembly 60 into the trough 58, the assembly 60 may be positioned. This permits positioning of the matrix member-gel slab assembly 60 in a first generally horizontal position such as shown in FIG. 5 with the gel immersed in the underlying buffer solution. Grasping of handle 72 and rotating of the assembly 60 permits positioning of the matrix member-gel slab assembly 60 in a different position which is not overlying trough 58 which is adapted to contain a buffer solution. It will be appreciated that when the matrix member-gel slab assembly 60 is in the position shown in FIG. 5 it is oriented generally horizontally and the gel is in contact with a buffer solution which is in underlying trough 58. A divider wall 82 is provided with an overflow sector 84 of reduced height to permit flow of the buffer into overflow pocket 86. By means of lower electrode 78 which is secured to post 76 and external contact 80 and is wired parallel to electrode 8 a suitable voltage may be applied. The proteins or other molecules will be caused to migrate upwardly through the gel into the individual wells which also have been provided with buffer solution. By imposing the desired AC voltage differential on the individual wells, independent processing of each protein in buffer solution sample is effected. These solutions can conveniently be removed from the respective wells with a hypodermic syringe or pipette.

Figure 7:
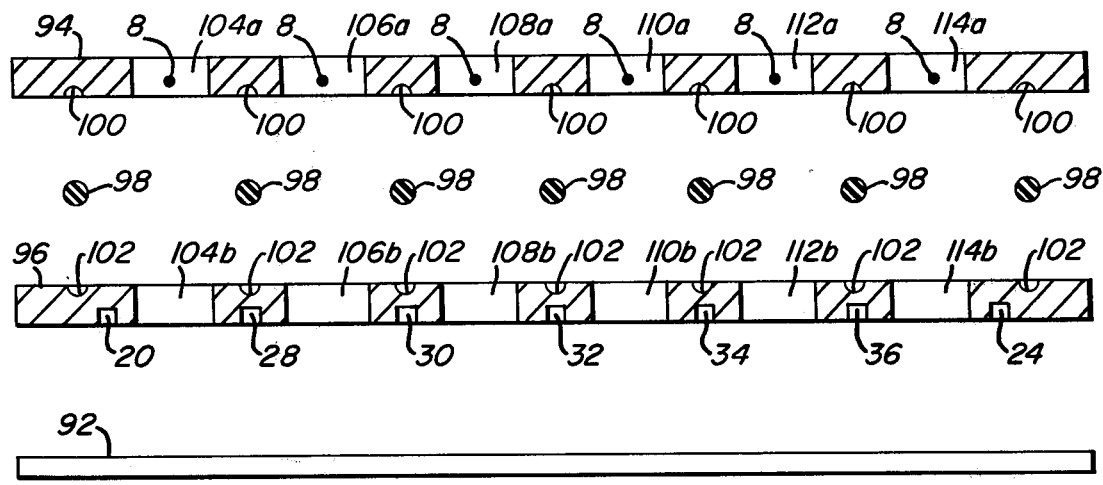
FIG. 7 is an exploded cross-sectional illustration of another embodiment of the invention.
Figure 7A:
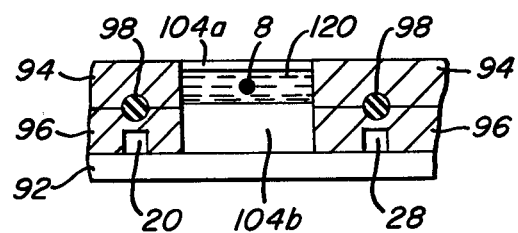
FIG. 7a is a fragmentary, partially schematic cross-sectional illustration of a portion of the embodiment of FIG. 7.

In the form shown in FIGS. 7 and 7a a gel slab 92 cooperates with a matrix member which is composed of an upper section 94, a lower section 96 and elongated interposed gasket means 98. In this embodiment it is contemplated that the upper section 94 may advantageously be reusable, while the lower section 96 may advantageously be disposable.

In use, the upper section 94 and the lower section 96 will be secured in intimate contact with each other with elongated gasket means 98 and transverse gasket means (not shown) which are preferably substantially coextensive with the regions of the openings in the sections 94, 96 being compressed between the upper section 94 and lower section 96. The gasket may advantageously be made from a suitable resiliently compressible material such as rubber, for example. In the form shown recesses 100, 102 receive and compress the gasket means 98. The gasket means effect sealed separation of the wells. During use, the assembly of the upper and lower sections 94, 96 may be secured by any suitable means (not shown) such as a number of channel shaped resilient metal clip members secured to the periphery or elongated channel shaped frame members, for example.

A series of channels 20, 24, 28, 30, 32, 34, 36 may be employed to secure the assembly to the gel slab 92 by vacuum means as described above.

The upper section 94 has a number of upper well segments 104a, 106a, 108a, 110a, 112a and 114a which cooperate respectively with lower well segments 104b, 106b, 108b, 110b, 112b and 114b of lower section 96 and gel slab 92 to define a plurality of wells. Electrode 8 passes through the wells.

An example of how the embodiment of FIGS. 7 and 7a might be employed will be considered. In connection with heart patients, blood serum electrophoresis is employed to determine whether a mycardial infarction exists. The lower well segments 104b, 106b, 108b, 110b, 112b and 114b are filled with gel rather than buffer. Different well segments 104b, 106b, 108b, 110b, 112b and 114b may have impregnated in the gel it contains a specific protein indicator such as an antibody, for example. Different well segments may have different protein indicators. Buffer 120 is provided in upper well segments 104a, 106a, 108a, 110a, 112a and 114a.

The assembly 94, 96, 98 is placed in intimate contact with gel slab 92 as by vacuum. The recovery electrophoresis procedure results in the proteins emerging from the gel slab 92 and entering into the wells to react with the protein indicators. The density of the formed bond after a predetermined elapsed time will indicate the amount of protein in a particular well.

This embodiment may be used for other purposes such as the testing for infectious diseases, for example. This apparatus permits rapid, economical and highly accurate results while permitting reuse of portions of the apparatus.

While for convenience of reference a preferred form showing elongated generally rectangular openings aligned in rows has been employed. It will be appreciated that other shapes and relative positionings of openings may readily be advantageously employed.

While for convenience of reference herein where specific examples have been provided reference has been made to proteins, this invention is not so limited and may be used in a wide range of electrophoresis recovery operations. Among the many additional uses are use in molecular studies in the medication purification of large molecules and in studies of purified drugs and their effect.

While for simplicity of reference herein specific disclosure of the preferred vacuum means of urging the matrix member and gel into intimate contact is provided. It will be appreciated that other means can be used.

The present invention through the preferred use of alternating current results in reduced undesired heating. The relatively short period required for recovery reduces heat generated in the system. Also, the trough 58 of buffer solution provides a reservoir for absorption of heat generated.

It will therefore be appreciated, that the present invention provides an economical and effective means for electrophoresis wherein a plurality of independent processing wells is established and the need for individual strips of gel or cellophane membranes has been totally eliminated. In addition to the speed with which these systems operate, undesired excessive dilution of specimens is avoided.

Whereas particular embodiments of the invention have been described above, for purposes of illustration it will be evident to those skilled in the art that numerous variations of the details may be made without departing from the invention as defined in the appended claims.

I claim:

1. Electrophoresis recovery apparatus comprising
a gel slab,
a matrix member having a first surface in generally surface-to-surface contact with said gel slab and a second surface,
said matrix member having a plurality of openings therein,
said matrix member overlying said gel slab,
said matrix member openings cooperating with said gel slab to define a number of generally upwardly open wells,
means for urging said gel slab and said matrix member into intimate contact,
electrode means passing through said wells,
electrical means for energizing said electrode means, and
reservoir means for providing buffer solution to said gel.

2. The electrophoresis recovery apparatus of claim 1 wherein
said means for urging said gel slab and said matrix member into intimate contact includes pressure differential creating means.

3. The electrophoresis recovery apparatus of claim 2 wherein
said pressure differential creating means includes channel means formed in said matrix member, pump means and conduit means connecting said pump means with said channel means, and
said channel means cooperating with said gel slab to define passageways.

4. The electrophoresis recovery apparatus of claim 3 wherein
said channel means formed in communication with said first surface of said matrix member.

5. The electrophoresis recovery apparatus of claim 1 wherein
said reservoir means has an upwardly open trough for holding buffer solution in contact with said gel slab when said gel slab is disposed in generally horizontal position.

6. The electrophoresis recovery apparatus of claim 5 wherein
said reservoir means has support means for supporting said matrix member-gel slab assembly in a generally horizontal position.

7. The electrophoresis recovery apparatus of claim 3 wherein at least a major portion of said channel means are spaced inwardly from the marginal edges of said matrix member.

8. The electrophoresis recovery apparatus of claim 4 wherein
said channel means has portions disposed in generally surrounding relationship with respect to said openings.

9. The electrophoresis recovery apparatus of claim 1 wherein
second electrode means are disposed within said reservoir means, and
said electrical means having means for energizing said second electrode means.

10. The electrophoresis recovery apparatus of claim 1 wherein
said electrode means and said second electrode means are wired in parallel.

11. The electrophoresis recovery apparatus of claim 9 wherein
said openings are of generally rectangular configuration and are disposed in rows.

12. The electrophoresis recovery apparatus of claim 11 wherein
said channel means have portions extending between adjacent rows of said openings.

13. The electrophoresis recovery apparatus of claim 1 wherein
said matrix member has a thickness of about 5 mm to 24 mm.

14. The electrophoresis recovery apparatus of claim 12 wherein
said gel is a polyacrylamide gel slab.

15. The electrophoresis recovery apparatus of claim 9 wherein
said electrical means are adapted to provide a low duty cycle alternating current.

16. The electrophoresis recovery apparatus of claim 1 wherein
said matrix member has an upper section and a lower section,
said upper section has a number of upper well segments, said lower section has a number of lower well segments generally aligned with said upper well segments and cooperating therewith and with said gel slab to define a series of wells.

17. The electrophoresis recovery apparatus of claim 16 wherein
protein indicator means are disposed within said lower well segments.

18. The electrophoresis recovery apparatus of claim 17 wherein
electrode means are disposed within said upper well segments.

19. The electrophoresis recovery apparatus of claim 16 wherein
gasket means interposed between said upper section and said lower section effect sealing of said wells to resist undesired communication therebetween.

* * * * *